(12) United States Patent (10) Patent No.: US 8,870,739 B2
LaRose et al. (45) Date of Patent: Oct. 28, 2014

(54) CONDUIT DEVICE FOR USE WITH A VENTRICULAR ASSIST DEVICE

(75) Inventors: Jeffrey A. LaRose, Parkland, FL (US); Douglas E. Godshall, Medfield, MA (US)

(73) Assignee: HeartWare, Inc., Miami Lakes, FL (US)

( * ) Notice: Subject to any disclaimer, the term of this patent is extended or adjusted under 35 U.S.C. 154(b) by 0 days.

(21) Appl. No.: 13/204,472

(22) Filed: Aug. 5, 2011

(65) Prior Publication Data

US 2012/0059212 A1 Mar. 8, 2012

Related U.S. Application Data

(60) Provisional application No. 61/401,033, filed on Aug. 6, 2010.

(51) Int. Cl.
*A61M 1/12* (2006.01)
(52) U.S. Cl.
CPC ........................................ *A61M 1/12* (2013.01)
USPC ............................................................ 600/16
(58) Field of Classification Search
USPC .............. 604/8–10; 623/3.1, 3.11, 3.16, 3.26; 600/16–18
See application file for complete search history.

(56) References Cited

U.S. PATENT DOCUMENTS

| 4,955,856 A | * | 9/1990 | Phillips | 600/16 |
| 6,346,071 B1 | * | 2/2002 | Mussivand | 600/16 |
| 6,726,648 B2 | | 4/2004 | Kaplon et al. | |
| 2002/0165426 A1 | * | 11/2002 | Sporer et al. | 600/16 |
| 2007/0299297 A1 | | 12/2007 | Jarvik | |

OTHER PUBLICATIONS

International Search Report issued by the International Searching Authority (ISA/US) on Dec. 6, 2011 in connection with International Application No. PCT/US11/46800.
Written Opinion of the International Searching Authority issued by the International Searching Authority (ISA/US) on Dec. 6, 2011 in connection with International Application No. PCT/US11/46800.

* cited by examiner

*Primary Examiner* — Amanda Patton
(74) *Attorney, Agent, or Firm* — Lerner, David, Littenberg, Krumholz & Mentlik, LLP

(57) ABSTRACT

The present invention is a conduit device designed to be placed within a wall of a heart, such as through a prepared opening or hole in the heart wall. The conduit is hollow and extends to form a sleeve over a portion of the heart pump, such as a VAD, which traverses the heart wall and enters a chamber of the heart. The conduit provides for a simplified and non-invasive approach to removal and/or replacement of the heart pump.

21 Claims, 7 Drawing Sheets

CONDUIT DEVICE FOR USE WITH A VENTRICULAR ASSIST DEVICE

CROSS-REFERENCE TO RELATED APPLICATIONS

This application claims the benefit of U.S. Provisional Application No. 61/401,033 filed Aug. 6, 2010, the contents of which are hereby incorporated by reference into this application.

BACKGROUND OF THE INVENTION

The present invention relates to components and methods used in connection with ventricular assist device and interaction with the anatomy of a human, namely the heart and blood flood therethrough.

In certain disease states, the heart lacks sufficient pumping capacity to meet the needs of the body. This inadequacy can be alleviated by providing a mechanical pump referred to herein as a heart pump or a ventricular assist device ("VAD"), one example of which is illustrated in FIG. 6, to supplement the pumping action of the heart. Considerable effort has been devoted to providing a VAD which can be implanted and which can remain in operation for months or years to keep the patient alive while the heart heals, or which can remain in operation permanently during the patient's lifetime if the heart does not heal, or which can keep the patient alive until a suitable donor heart becomes available.

The VAD is typically connected to the heart, most commonly to the left ventricle. Typically, one end of an outflow tube is connected to the VAD and the other end is connected to the aorta. Once connected, the VAD and the heart both pump blood from the left ventricle to the ascending or descending aorta to improve blood flow. Alternatively, a VAD may be connected to the ventricle to assist the heart in pumping blood into pulmonary arteries.

The VAD 82 typically is connected to the heart through the use of a sewing ring or a VAD connector 50 (see FIG. 6), as disclosed in U.S. Published Patent Application Nos. 2004/0171905 and 2007/0134993, the disclosures of which are both hereby incorporated by reference herein as if fully set forth herein. The VAD connector may be in the shape of a ring and is attached to the outer surface of the heart, commonly through the use of sutures. A separate surgical tool is then used to cut or core a hole in the ventricle centered within the VAD connector. An inflow tube 84 (FIG. 6) extending from the VAD is inserted through the hole in the left ventricle. The VAD is then attached to the VAD connector such that the inflow tube 84 of the VAD is positioned within the central opening of the VAD connector 50. The VAD connector is used to clamp the inflow tube and thereby hold the VAD in position relative to the heart and form a seal around the inflow tube.

However, such connectors and configurations can potentially cause problems when the VAD is removed and/or replaced with a new VAD. For example, upon implantation of a VAD, using the above configurations, the heart wall, and related tissues, heal around the VAD structure. Once the VAD requires replacement, and the VAD structure is separated from the healed tissue, the risk of renewed bleeding or embolization may occur. Moreover, upon implantation of the new VAD, the healing process must recur, risking infection, prolonged bleeding, or other complications.

An additional drawback to the current configurations, of above, is that, during initial placement of the VAD or replacement of the VAD, the opening in the heart wall is open and thus blood from the heart may exit from the opening. To avoid massive blood loss, the patient may be subjected to cardioplegia (temporary stoppage of the heart), cardiopulmonary bypass, or both during implantation of the VAD, during removal of the VAD, or during implantation of a replacement VAD. Moreover, this hole in the heart wall may allow the inflow, through the hole and into the heart, of outside air, which can also cause complications for the patient.

For at least these reasons, a new device capable of securing a VAD to heart tissue, or other cardiovascular tissue, while alleviating or eliminating many of the issues above, is needed.

BRIEF SUMMARY OF THE INVENTION

In one embodiment, the present invention may include a conduit designed to be placed within a wall of a heart, such as through a prepared opening or hole in the heart wall. The conduit is hollow and extends to form a sleeve over a portion of the heart pump, such as a VAD, which traverses the heart wall and enters a chamber of the heart. The conduit provides for a simplified and noninvasive approach to removal and/or replacement of the heart pump.

In another embodiment, the present invention may include a conduit device adapted for placement within a wall of a heart, comprising a hollow generally cylindrical body, having an interior bore, the body being adapted for engagement with a portion of a heart pump and an exterior surface, the body comprising a tissue-growth promoting material adapted to promote growth of tissue on the exterior surface.

Further, the conduit device may be adapted to be fixedly connected to an implant connector, and the implant connector may be adapted for removable engagement with the heart pump. The conduit device may be substantially cylindrical, or may include a taper along at least a portion of the length. Additionally, the body may have a leading end adapted for positioning within the heart, the device further may include a coring projection extending from the leading end of the body.

Moreover, the conduit device may include a valve fixedly secured within the interior bore of the conduit device and may have an open position in which the valve occludes the bore and a closed position in which the valve does not occlude the bore. In one example, the valve may be a one-way valve and include a plurality of closure elements resiliently biased towards one another, and further the body may be adapted to engage the portion of the pump so that the portion projects between the closure elements. These closure elements may form a seal around the portion of the pump when the portion is received in the bore and through the valve.

In one example, the conduit device may be secured to the wall of the heart by a VAD connector and an at least one length of suture. In another example, the conduit device may be secured to the wall of the heart by a flange and an at least one length of suture. In yet another example, the conduit device may be secured to the wall of the heart by a sewing ring and an at least one length of suture.

Moreover, the body may have a leading end adapted for placement within the heart and a trailing end, and the body may be adapted to engage a portion of the pump so that the portion of the pump may extend into the bore from the trailing end.

In a further embodiment, the present invention may include a conduit device adapted for placement within a wall of a heart, comprising a hollow generally cylindrical body, having an interior bore and a valve, the body being adapted for engagement with an inflow tube extending from a heart pump, through the bore and the valve, and to a chamber of the heart, wherein the valve is adapted to minimize blood flow out of the heart and the conduit device is adapted to be fixedly connected to an implant connector, and the implant connector is adapted for removable engagement with the heart pump.

Further, the conduit body may include a tissue-growth promoting material. Also, the inflow tube may have a length which is longer than the length of the conduit device.

In yet another embodiment, the present invention may include a device for assisting the flow of blood through at least a portion of the heart, the device comprising the combination of a heart pump and a conduit device of any of the disclosed embodiments, a portion of the heart pump being engaged with the interior bore of the conduit device.

For example, the portion of the heart pump may be an inflow tube extending from the pump, through the interior bore, and to a chamber of the heart. The inflow tube may further have a length which is longer than the length of the conduit device. Alternatively, the portion of the heart pump may be a body of an axial flow pump. The device may further include an implant connector, wherein the conduit device may be fixedly connected to the implant connector, and the implant connector may be removably engaged with the heart pump. The implant connector may be a flange, a VAD connector, a sewing ring, or any combination thereof.

In another embodiment, the present invention includes a method for treating a heart condition, which comprises accessing a portion of a wall of a heart, through either open surgery or arthroscopic methods, positioning a conduit device through an access hole through the heart wall, securing the conduit device to the heart wall, inserting a portion of a heart pump through the conduit device, and releasably securing the heart pump to the conduit device. The method may further include the step of removing the heart pump by accessing the implant site, releasing the heart pump from the implant connector and conduit device, and removing the heart pump from the heart and conduit device. The method may then further include the step of inserting a portion of a new heart pump through the conduit device, and releasably securing the new heart pump to the conduit device using the implant connector. Alternatively, once the heart pump has been removed, the method may include implanting a plug within the conduit device to substantially seal the interior bore of the conduit device.

BRIEF DESCRIPTION OF THE DRAWINGS

FIGS. 2A and 2B illustrate another embodiment of a conduit device of the present invention, wherein FIG. 2A shows a valve in a closed position and FIG. 2B shows the valve in an open position with an inflow tube from a heart pump positioned therethrough.

DETAILED DESCRIPTION

Figure 1:
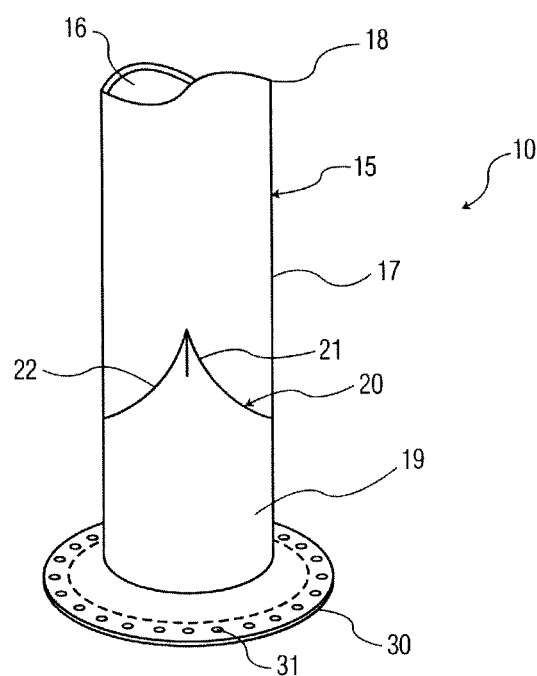
FIG. 1 illustrates one embodiment of a conduit device of the present invention.

In one embodiment, as illustrated in FIG. 1, a conduit device 10 includes a hollow body 15 which defines an interior bore 16. Device 10 may further include at least one of a valve 20 and an implant connector, such as flange 30. The device 10 is dimensioned to be positioned adjacent to, or within, the heart. For example, device 10 may be positioned within a prepared hole through the wall of the heart which creates a passageway from the outside of the heart and into at least one of the chambers of the heart, such as the left ventricle. While this positioning of device 10 will be the exemplary location in the below embodiments, it is envisioned that device 10 may be used in other locations within the cardiovascular system of a mammal where a heart pump or other such device is in need.

The hollow body 15, defining interior bore 16 therethrough, has a generally cylindrical shape along its length. Body 15 is adapted for engagement with a portion of a heart pump, such as an inflow tube (for example, illustrated as inflow tube 84 in FIG. 6) which may be positioned within the interior bore 16 (see FIG. 7). The body 15 has a leading portion 18 and a trailing portion 19. The leading portion 18 is adapted to be positioned within the heart, while the trailing portion 19 is adapted to be positioned at or adjacent to a wall of the heart and secured to both a portion of the heart pump and to an outer surface of the heart wall optionally using, for example, an implant connector such as flange 30.

The body 15 may include an outer surface 17 capable of promoting tissue growth, or a neo-intimal linking, along at least a portion of the length of the body 15. The tissue-growth, however, may be limited to only the outer surface 17 of body 15, such that the interior bore 16 is substantially protected from tissue in-growth. This may also protect structures positioned within bore 16 from tissue in-growth. Such limited in-growth may be accomplished by forming a growth-promoting layer or material on the outer surface 17, with a substantially impermeable underlayer beneath the growth-promoting layer. The tissue-growth promoting layer or material may include, for example, a texture suitable for tissue in-growth created by sintered titanium microspheres, or by the application of a textile such as Dacron® PET. The impermeable layer may be any material capable of substantially preventing tissue in-growth, such as high-density polyethylene or the like, as is known in the art.

The growth-promoting layer of the conduit device 10 may be adapted to promote wound healing at the contact area of the wall of the heart and the outer surface 17, though, the growth promoting layer may extend along any portion of the length of body 15. The tissue in-growth at the contact area of the wall of the heart and the outer surface 17 may provide additional stability to the secure connection between body 15 and the heart wall. This stable connection may promote hemostasis and may decrease the risk of embolization at the wound site, particularly during removal and/or replacement of the heart pump.

The body 15 may be rigid or pliable, depending on the intended use of the device 10. For example, if the device 10 is intended for placement through a heart wall, the body 15 may have a certain degree of pliablility such that the body 15 is capable of expanding, contracting, and bending due to the movement of the heart and heart wall as the heart beats. Such a pliable structure may also provide for a better seal between the body 15 and the portion of the heart pump within the interior bore 16. For example, the diameter of the interior bore 16 may be substantially the same, or slightly smaller than, the diameter of the portion of the heart pump, such that insertion of the portion of the heart pump into the interior bore 16 causes the body 15 to expand, which may then create a force exerted by the body 15 to return to its original diameter. Such elasticity of the body 15 may result in a better seal between the body and the portion of the heart pump within the interior bore. As such, for a body 15 which is intended to be pliable, the body 15 may generally be constructed of a textile or other fabric material, such as braided polymeric filaments. Suitable materials for a rigid body 15 may be high density plastics and/or metals.

Figure 6:
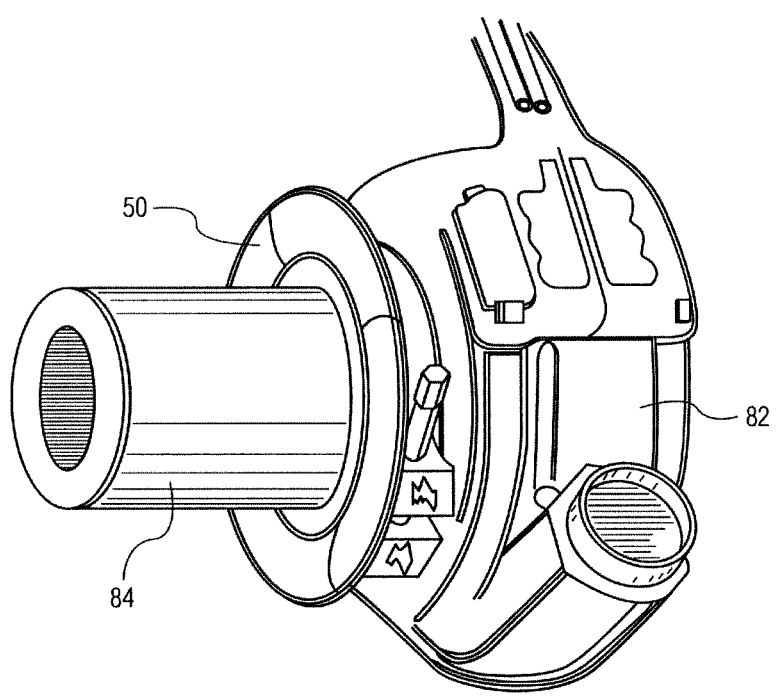
FIG. 6 illustrates one example of a heart pump, or VAD, known in the prior art.

Device 10 may also include an implant connector, such as flange 30, which may be fixedly positioned on or adjacent to the trailing portion 19 of body 15 such that trailing portion 19 of device 10 can further securely engage to, for example, a heart pump or a VAD connector (see FIG. 6). The flange 30 may be secured to the body 15 through a suture, an adhesive, or the like, or may be formed or woven along with the body itself, as a unitary structure. The implant connector may alternatively be a typical sewing ring or the VAD connector itself, either of which may be secured to the body 15 using a suture, adhesive, or the like. In any of these alternatives, the implant connector fixedly secures the body 15 to tissue, such as at the contact area with the wall of the heart, using at least one length of suture using, for example, suture throughholes 31 as on flange 30, though such throughholes may also be present on the sewing ring or VAD connector, if used.

The implant connector may further provide for removable engagement with the VAD. Thus, the device 10 and implant connector remain engaged to the heart, while the heart pump is removable therefrom. Additionally, suture throughholes 31 may also be used to secure flange 30 to the VAD connector in addition to the heart tissue. In this arrangement, the VAD connector may also be fixedly secured to the flange 30, such that the body 15 with flange 30, along with the VAD connector, is held in place in the heart by the flange sutured to the heart tissue, as well as by the tissue in-growth, while the heart pump is removable therefrom.

Figure 5:
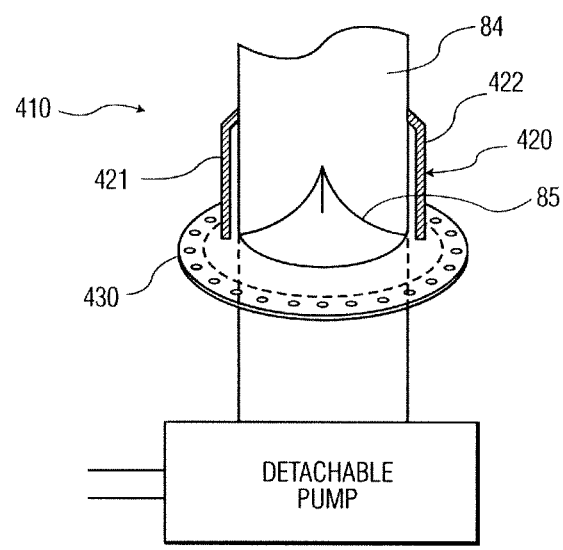
FIG. 5 illustrates one embodiment of a combination of a conduit device and a heart pump having an inflow tube.

The device 10 may further include a valve 20 positioned within the interior bore 16 of body 15. The valve 20 is fixedly secured to the interior of the body 15 such that the valve 20 remains in position even when, for example, blood or inflow tube 84 passes through the interior bore 16 and contacts valve 20. For example, valve 20 may be sewn to the interior of body 15, or alternatively, an adhesive may be used, or the like. Of course, valve 20 and body 15 may also be manufactured as a single, continuous structure. Valve 20 includes at least an open position in which the valve occludes the bore and a closed position in which the valve does not occlude the bore. Valve 20 may be a one-way valve and may include a plurality of closure elements 21, 22 resiliently biased towards one another such that they allow blood, an inflow tube 84, or the like to pass in one direction but prevent blood from traveling in the other direction. Similarly, the resilient bias of the closure elements may, for example, engage the inflow tube 84 of the heart pump so that the inflow tube projects between the closure elements and the closure elements create a tight connection to substantially seal around the inflow tube to substantially prevent leakage, as illustrated in FIG. 5, for example. The valve may include more than just two closure elements 21, 22, and may have three or more elements, all of which function similar to elements 21, 22. Similarly, subsequent to the implantation of the device 10 into, for example, the wall of the heart, but prior to the insertion of the heart pump, for example the inflow tube, into the interior bore 16, the valve 20 may substantially prevent the flow of blood from the heart via the body 15.

The valve 20 may be any type of valve suitable for the above purposes. FIGS. 1 and 5 illustrate valves having three-dimensional closure elements similar in design to a natural heart valve or similar one-way type valve. Alternative embodiments of valves suitable for use in the conduit device are also disclosed below, though it is envisioned that other shapes and types of one-way valves may also be incorporated.

Figure 7:
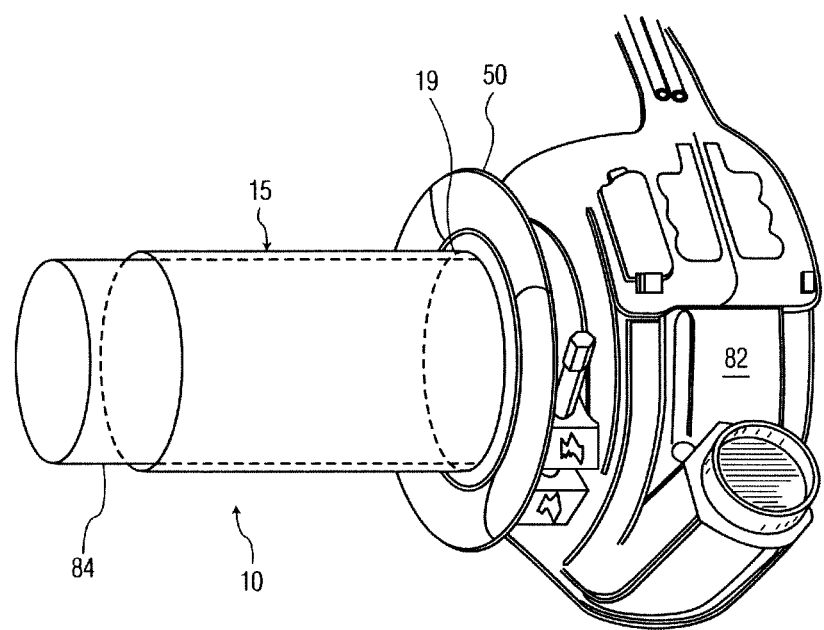
FIG. 7 illustrates yet another embodiment of a combination of one embodiment of a conduit device of the present invention and the heart pump of FIG. 6.

FIG. 7 illustrates a further embodiment of a device for assisting the flow of blood through at least a portion of the heart including the combination of a heart pump 82 and a conduit 10 similar to conduit 10 of FIG. 1, though the implant connector is VAD connector 50 rather than flange 30. Of course, flange 30 may also be included to engage the body 15, heart wall and VAD connector 50 to one another (or, a sewing ring may replace the VAD connector and/or the flange). Additionally, valve 20 has been removed for clarity, though in this combination the valve would be substantially open and the closure elements 21, 22 would be adjacent to an inner surface of the interior bore 16.

As FIG. 7 illustrates, an inflow tube 84 of the heart pump 82 may be positioned within the interior bore 16 of body 15 such that, if body 15 is secured through a heart wall, the inflow tube extends from the distal end 19 of the body 15, through the body 15, and into the heart, such as a chamber of the heart. The length of the inflow tube 84 may be longer than the body 15, such that it extends further into the heart than the body 15. The pump may be removeably secured to the wall of the heart through VAD connector 50, and the VAD connector is in turn fixedly secured to both the body 15 and the wall of the heart (see FIG. 8).

Figure 8:
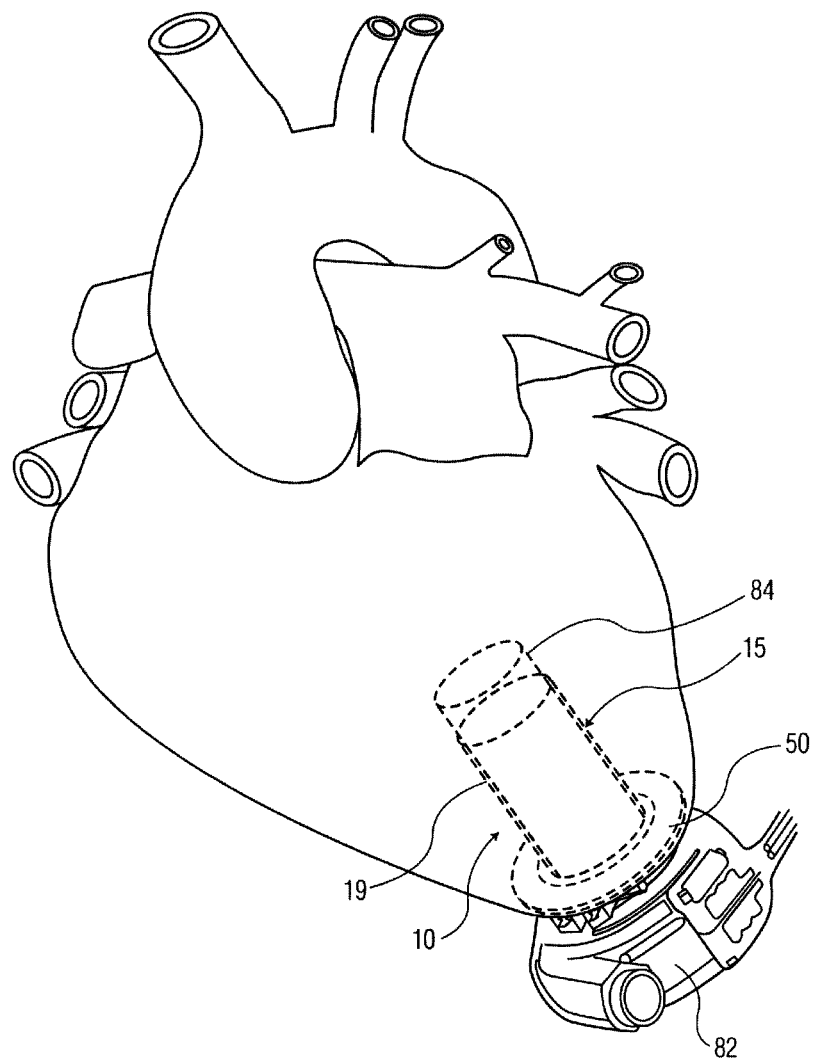
FIG. 8 illustrates the placement of the combination of FIG. 7 through a wall of a heart.

FIG. 8 illustrates this embodiment in position on the wall of the heart, with inflow tube 84 protruding into the left ventricle. In this embodiment, the heart wall, body 15, and VAD connector 50 are all secured to one another, through the use of an at least one length of suture, and VAD connector 50 and heart pump 82 are releasably secured to one another.

In use, the conduit device 10 provides for a more manageable connection between the heart pump and the heart tissue. The conduit provides an intermediate layer between the heart tissue and the heart pump, thus minimizing possible interaction between the heart pump and heart tissue during removal or replacement of the heart pump.

For example, to further the embodiment of FIGS. 7 and 8, the present invention may also include an embodiment of a method for treating a heart condition, which includes accessing a portion of a wall of a heart, through either open surgery or arthroscopic methods, positioning a conduit device 10 through an access hole through the heart wall, securing the conduit device 10 to the heart wall, inserting a portion of a heart pump through the conduit device, and releasably securing the heart pump to the conduit device. The access hole through the heart wall may be created prior to positioning the conduit device through the hole, or in conjunction with positioning the conduit device through the hole. Once the conduit device 10 is positioned through the heart wall, the device is secured to the heart wall by, for example, suturing the implant connector of the device 10 to an outer surface of the heart wall adjacent to the access hole. Further, such securing of the device may allow tissue growth to occur between adjacent heart wall tissue and the outer surface 17 of the conduit device 10, and possibly on the implant connector itself.

Once the conduit device is in place, the heart pump may be positioned within the conduit device. For example, the heart pump may include an inflow tube 84, which may be inserted into the conduit device 10 such that it passes through the device and enters into the inner volume of a chamber of the heart. The heart pump is then releasably secured to the conduit device using the implant connector such as, for example, the VAD connector 50, a flange and/or a sewing ring. As illustrated in FIGS. 7 and 8, the VAD connector 50 is fixedly secured to the device 10 and the heart wall, and the heart pump is releasably secured to the VAD connector 50.

The method may further include the step of removing the heart pump, once the heart pump is no longer working properly or no longer needed, by accessing the implant site, releasing the heart pump from the implant connector and conduit device, and removing the heart pump from the heart and conduit device.

If a new heart pump is needed, the method may then further include the step of inserting a portion of a new heart pump through the conduit device, and releasably securing the new heart pump to the conduit device using the implant connector. For example, using the structure disclosed in FIG. 8, VAD connector 50 is loosened or unlocked from its connection to the heart pump, typically to inflow tube 84, and the heart pump and inflow tube are withdrawn from the device 10. Device 10 remains in place through the heart wall. The valve (not shown) closes within the interior bore of the conduit and prevents backflow of blood out of the device 10. A new pump with a new inflow tube is then implanted in similar manner, by placing inflow tube through device 10, causing valve 20 to re-open, and tightening VAD connector 50 onto the new pump. This step may be replicated as necessary as the conduit device minimizes possible trauma to the heart tissue by the removal and replacement of heart pumps into the heart. Of course, if another pump is not going to be implanted, the conduit device may remain in the heart tissue and a plug of suitable geometry may be placed within the device 10 to prevent leakage of blood through the conduit device. The plug may fill substantially the entire length of the interior bore, or may only fill one end of the conduit device.

The inclusion of a valve into the device 10 may limit the need for bypass during such a surgical method because the blood will not flow out of the device due to the one way valve, thus substantially reducing, if not all together eliminating, the need for the patient to be placed on bypass during implantation of the device 10. Of course, bypass may be utilized if desired.

The valve may also reduce the need for de-airing, or alternatively simplifying the de-airing process, the pump prior to final implantation because the valve may limit the amount of air in the device 10, and therefore limit the amount of air present in the device 10 upon exposure to air during implantation or replacement of a pump. Such limitation of exposure also may reduce possible complications associated with such exposure. Previously, a surgeon would have had to de-air a larger volume because, during pump replacement, the interior of the heart was open to the atmosphere. The device 10, however, includes a valve which limits the exposure of the interior of the heart to the outside atmosphere.

Figure 2A:
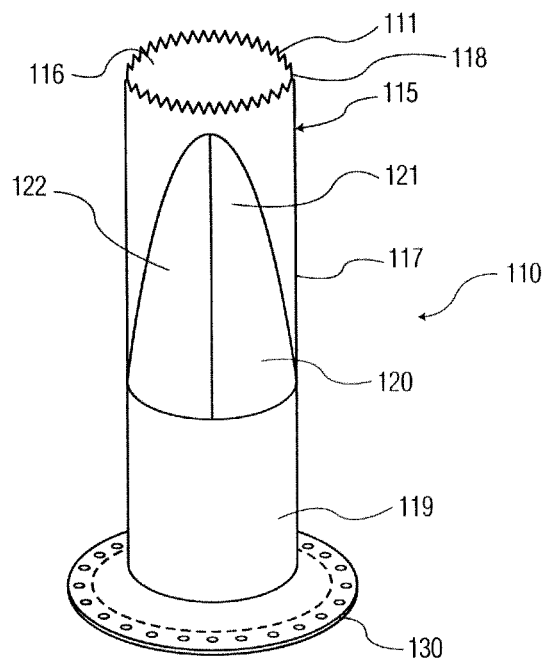
Figure 2B:
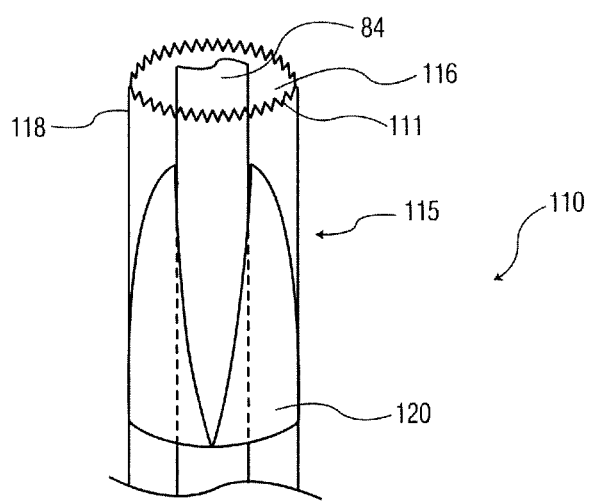

FIGS. 2A and 2B illustrate another embodiment of the conduit device 110, in which the leading end 118 of the body 115 is capable of being positioned within the heart, and further includes a coring projection 111 extending therefrom. Coring projection 111 may be used to implant the device 110, such as by coring a hole through the wall of the heart, through which the body 115 will be secured. The resulting core is removed from the heart wall by retrieving the core through the interior bore 116 of the body 115 using an appropriate instrument. In alternative arrangements, the leading end 118 of body 115 may be smooth, or be of a non-cutting shape, and a separate coring device may be positioned through the interior bore 116, or may be inserted through the heart wall prior to the insertion of the device 110. However, the use of coring projection 111 may simplify this type of surgery by limiting the number of instruments necessary for implantation of the device 110. The resulting hole through the heart wall may be substantially the same size as the outer diameter of body 115, or may be slightly smaller than this outer diameter, to ensure a tight, substantially sealed fit. Such a tight fit may minimize leaking between the tissue wound and the body 115, and may further promote healing of the tissue wound. Additionally, combining the coring and implantation of the device into a single step may provide improved accuracy in alignment of the device 110 with the hole in the heart wall.

Coring projection 111 may be used in conjunction with a valve, such as valve 120 illustrated as a "duck-bill" shaped valve which may include two elongated, pliable closure elements capable of substantially sealing around an inflow tube of a heart pump, additional instrumentation, or other such structure, positioned through the valve. In this embodiment, a core capturing instrument (not shown) would be positioned through valve 120 to the leading end 118 of the body 115, in order to capture the core after it has been cut by coring projection 111. Alternatively, a separate coring instrument may be placed within bore 116, and through valve 120. The valve 120 would substantially seal around any instrument passing therethrough until the core and instrument are removed from valve 120, causing the valve 120 to close and seal the bore 116 thus preventing blood from exiting the heart.

Figure 3A:
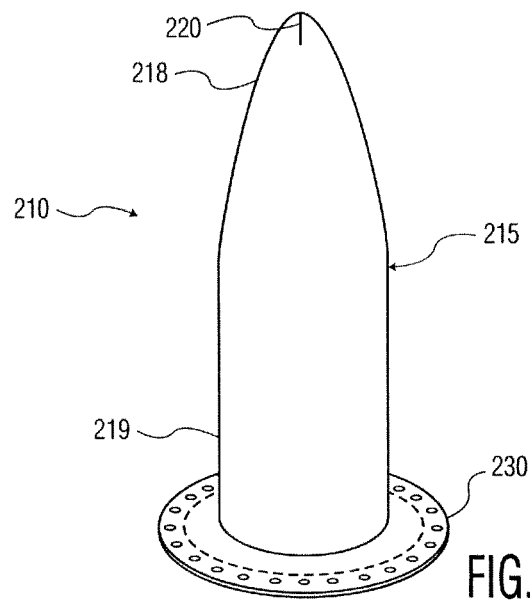
FIGS. 3A and 3B illustrate a further embodiment of a conduit device of the present invention.
Figure 3B:
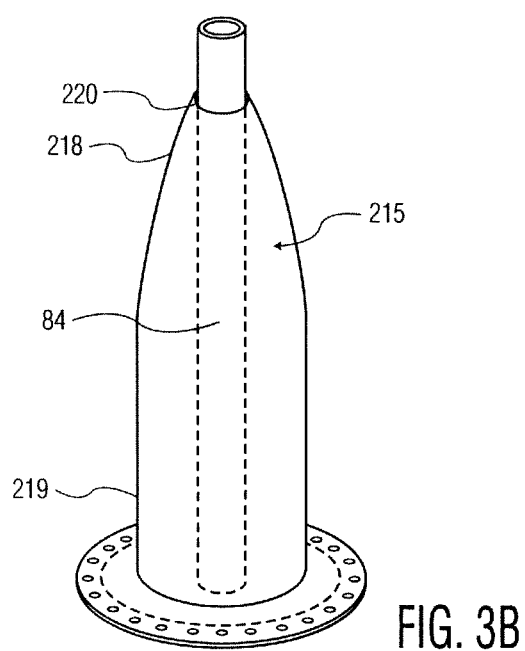

FIGS. 3A and 3B illustrate a further embodiment of the conduit device 210 which includes a hollow body 215 having a substantially cylindrical shape along at least a portion 219 of its length, and the remaining portion 218 of its length having a substantially conical shape. As discussed above, the body 215 may be expandable to accommodate an inflow tube 84 from a heart pump therethrough. Therefore, in this embodiment, the leading end of the substantially conical portion 218 of the body 215 may be adapted to act as a valve 220, such that the leading end of the conical portion is substantially closed, as in FIG. 3A to prevent backflow of blood from the heart. As the inflow tube 84 is passed through body 215 and out this leading end of the conical portion 218, the leading end expands around the inflow tube, as in FIG. 3B. The elasticity of conical portion 218 may prevent leakage between the conical portion and the inflow tube due to the tendency of the conical portion 218 to contract back to its original shape with a smaller diameter, thus forming a tight, sealed fit between the body 215 and inflow tube 84.

Figure 4:
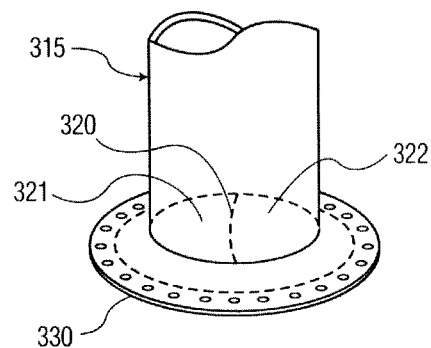
FIG. 4 illustrates an alternative embodiment of a valve of a conduit device of the present invention.

FIG. 4 illustrates yet another embodiment of a valve for use in the conduit device. Valve 320 is a substantially flat valve which may include a membrane with a slit therethrough, forming elements 321 and 322. As to FIG. 4, in order to prevent back-out of blood through the valve from the heart, the slit may include an overlap of material which may maintain a seal, during periods of back pressure from the blood coming from the heart and entering the interior bore of the body, by preventing elements 321 and 322 from inverting.

As illustrated in FIG. 5, in a further embodiment, a device for assisting the flow of blood through at least a portion of the heart includes the combination of a detachable heart pump and a conduit 410. Much like the embodiment illustrated in FIG. 7, the conduit includes valve 420 (shown in cross-section) and an implant connector (flange 430), but the body of conduit 410 only has a length substantially the width of the flange 430. Thus, the conduit is positioned essentially only on the outer wall of the heart, and secured thereto. In effect, conduit 410 is an access doorway for a pump to gain access to the interior of the heart, while still providing a layer between the inflow tube of the heart pump and the heart wall at the opening in the heart wall. The inflow tube 84 of the pump is then placed through the valve, thus pushing elements 421 and 422 away from their original position, and the inflow tube 84 thus passes into the heart. As in other embodiments, elements 421 and 422 may have a bias towards returning to their original position, and thus may press against the outside surface of inflow tube 84 to provide a seal to inhibit leakage. It may be desirable to prevent tissue growth on the valve 420 itself, and thus the valve may be constructed of a suitable material to prevent tissue in-growth on the valve itself. As illustrated in this embodiment, the inflow tube may also include a valve 85, similar to those disclosed herein, to assist in preventing leakage during pump detachment.

In yet another embodiment (not shown), the body of the conduit device may itself act as the inflow tube of the heart pump, such that the trailing end of the body attaches directly to the pump body, or separate VAD connector (if present), and the blood flows directly through the interior bore of the body, without an inflow tube of the pump being present. In this embodiment, the body of the conduit device would be releasably secured to the pump body at its trailing end through the separate VAD connector or alternatively through a press-fit or other connection with the heart pump. Similar to the above embodiments, while the outer surface of the body of the conduit device may promote tissue-growth, the inner surface of the interior bore of the body may be of a material, or include suitable treatment, to prevent the in-growth of tissue, or further to prevent adhesion of blood onto its surface.

In yet another embodiment, the pump may be an axial flow pump (not shown), which is sized to be positioned substantially completely within the interior bore of the conduit device body. In this embodiment, the pump itself may pass through the bore, through a valve (if present), and a portion may pass into the interior of the heart. Thus, such a pump may not have an inflow tube, and instead the pump itself would be secured within the interior bore using, for example, a connector between the trailing end of the body of the conduit device and the axial flow pump.

Alternatively, in any of the above embodiments, after the conduit device is in place within the heart, but a heart pump is not attached, a plug (not shown) may instead be placed within the interior bore of the body. The plug may also be used to replace the heart pump if it is no longer needed or if it is removed for a period of time. One such plug is disclosed in U.S. Published Application No. 2009/0171136, the disclosure of which is hereby incorporated by reference herein as if fully set forth herein. The plug may be secured to the implant connector and/or the body of the conduit device.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A conduit device adapted for placement through a wall of a heart, comprising:
a hollow generally cylindrical body, having an interior bore defining an inwardly-facing interior surface, an outwardly-facing exterior surface opposite from the interior surface, a first end and second end,
the body being adapted for removable engagement with a portion of a heart pump at the first end, for engagement with the wall of the heart at the first end, and for placement through the wall of the heart such that the second end and at least a portion of the exterior surface are within a chamber of the heart, the body comprising a tissue-growth promoting material adapted to promote growth of tissue on the exterior surface.

2. The conduit device of claim 1, wherein the portion of the heart pump is removable from the conduit device.

3. The conduit device of claim 1, wherein the first end of the body of the conduit device includes an implant connector, and the implant connector is adapted for removable engagement with the heart pump.

4. The conduit device of claim 1, wherein the material comprises sintered titanium microspheres or a growth-promoting textile.

5. The conduit device of claim 1, wherein the conduit device is substantially cylindrical.

6. The conduit device of claim 1, wherein the conduit device includes a taper along at least a portion of the length.

7. The conduit device of claim 1, further comprising a coring projection extending from the leading second end of the body.

8. The conduit device of claim 1, further comprising a valve fixedly secured within the interior bore of the conduit and having an open position in which the valve occludes the bore and a closed position in which the valve does not occlude the bore.

9. The conduit device of claim 8, wherein the valve comprises a one-way valve and includes a plurality of closure elements resiliently biased towards one another and wherein the body is adapted to engage the portion of the pump so that the portion projects between the closure elements.

10. The conduit device of claim 9, wherein the closure elements are adapted to form a seal around the portion of the pump when the portion is received in the bore and through the valve.

11. The conduit device of claim 8, wherein the valve has a duckbill-shape.

12. The conduit device of claim 1, wherein the conduit device is secured to the wall of the heart by an implant connector and an at least one length of suture.

13. The conduit device of claim 1, wherein the portion of the conduit device which is adapted for placement through the wall of the heart is adapted for insertion of at least a portion of the pump into the bore thereof from the first end of the conduit device, the conduit device being adapted for a configuration in which the portion of the conduit device and the at least a portion of the pump are within the chamber of the heart.

14. A conduit device adapted for placement through a wall of a heart, comprising a hollow generally cylindrical body, having a first end including an implant connector, a second end, an interior bore defining an inwardly-facing interior surface, an outwardly-facing exterior surface opposite from the interior surface, and a valve, the body being adapted for engagement with an inflow tube extending from a heart pump, through the bore and the valve, and to a chamber of the heart, and for placement through the wall of the heart such that the first end engages the wall of the heart and the second end and at least a portion of the exterior surface are within the chamber of the heart, wherein the valve is adapted to minimize blood flow out of the heart and the implant connector is adapted for removable engagement with the heart pump.

15. The conduit device of claim 14, wherein the body comprises a tissue-growth promoting material.

16. The conduit device of claim 14, wherein the inflow tube has a length which is longer than the length of the conduit device.

17. A device for assisting the flow of blood through at least a portion of the heart, the device comprising the combination of a heart pump and a conduit device of claim 14 or claim 15, a portion of the heart pump being engaged with the interior bore of the conduit device.

18. The device of claim 17, wherein the portion of the heart pump comprises an inflow tube extending from the pump, through the interior bore, and to a chamber of the heart.

19. The device of claim 18, wherein the inflow tube has a length which is longer than the length of the conduit device.

20. The device of claim 17, wherein the portion of the heart pump comprises a body of an axial flow pump.

21. The conduit device of claim 14, wherein the portion of the conduit device which is adapted for placement through the wall of the heart is adapted for insertion of at least a portion of the pump into the bore thereof from the first end of the conduit device, the conduit device being adapted for a configuration in which the portion of the conduit device and the at least a portion of the pump are within the chamber of the heart.

* * * * *

UNITED STATES PATENT AND TRADEMARK OFFICE
CERTIFICATE OF CORRECTION

| | | |
|---|---|---|
| PATENT NO. | : 8,870,739 B2 | Page 1 of 1 |
| APPLICATION NO. | : 13/204472 | |
| DATED | : October 28, 2014 | |
| INVENTOR(S) | : Jeffrey A. LaRose and Douglas E. Godshall | |

It is certified that error appears in the above-identified patent and that said Letters Patent is hereby corrected as shown below:

Column 10, line 62, "claim 14" should read --claim 1--

Signed and Sealed this
Ninth Day of August, 2016

Michelle K. Lee
*Director of the United States Patent and Trademark Office*